United States Patent [19]

Correia et al.

[11] Patent Number: 5,399,796
[45] Date of Patent: Mar. 21, 1995

[54] PURIFICATION OF 1,1-DICHLORO-1-FLUOROETHANE

[75] Inventors: Yves Correia, Chateau-Arnoux; Michel Bergougnan, Pierre-Benite; Jean Lesparre, Volonne; Sylvain Perdrieux, Vernaison, all of France

[73] Assignee: Societe Atochem, Puteaux, France

[21] Appl. No.: 158,474

[22] Filed: Nov. 29, 1993

Related U.S. Application Data

[63] Continuation of Ser. No. 46,883, Apr. 14, 1993, abandoned, which is a continuation of Ser. No. 924,604, Jul. 27, 1992, abandoned, which is a continuation of Ser. No. 580,973, Sep. 12, 1990, abandoned.

[30] Foreign Application Priority Data

Sep. 12, 1989 [FR] France .................. 89 11882

[51] Int. Cl.6 .................................. C07C 17/38
[52] U.S. Cl. .................................. 570/178; 570/177
[58] Field of Search .................. 570/177, 178

[56] References Cited

U.S. PATENT DOCUMENTS

| | | |
|---|---|---|
| 2,560,838 | 7/1951 | Arnold . |
| 2,637,747 | 5/1953 | McBee . |
| 4,028,426 | 6/1977 | Mansell . |
| 4,948,479 | 8/1990 | Brooks et al. . |
| 5,105,033 | 4/1992 | Swearingen ............... 570/166 |

FOREIGN PATENT DOCUMENTS

| | | |
|---|---|---|
| 0399705A1 | 11/1990 | European Pat. Off. . |
| 627773 | 8/1949 | United Kingdom . |
| 1401541 | 7/1975 | United Kingdom ........... 570/177 |

Primary Examiner—Alan Siegel
Attorney, Agent, or Firm—Morgan & Finnegan

[57] ABSTRACT

This invention relates to a process for the purification of 1,1-dichloro-1-fluorethane.

To remove unsaturated impurities such as 1,1-dichloroethylene and dichloracetylene the crude 1,1-dichloro-1-fluoroethane is subjected to the action of chlorine and/or of a hydracid. This treatment is carried out in the presence of a Lewis acid, or, only in the case of chlorine, by photochemical catalysis.

6 Claims, No Drawings

PURIFICATION OF 1,1-DICHLORO-1-FLUOROETHANE

This is a continuation of application Ser. No. 08/046,883, filed on Apr. 14, 1993, now abandoned, which a continuation of application Ser. No. 07/924,604, filed on Jul. 27, 1992, now abandoned, which is a continuation of Ser. No. 07/580,973, filed on Sep. 12, 1990, now abandoned.

FIELD OF THE INVENTION

The invention relates to the field of chlorofluorohydrocarbons and its subject is more particularly a process for the purification of 1,1-dichloro-1-fluoroethane (also known by the designation 141 b).

BACKGROUND OF THE INVENTION

This compound, prepared from 1,1-dichloro-ethylene (A. E. Feiring, J. Fluorine Chem., 14(1), 7–18 (1979)) or from 1,1,1-trichloroethane (patent no. DE 2,137,806) contains as impurities unsaturated chloro or chlorofluoro compounds which are undesirable in the use of 1,1-dichloro-1-fluoroethane. The most inconvenient of these unsaturated impurities are 1,1-dichloroethylene and dichloroacetylene whose boiling points (31.7° C. and 33° C. respectively) lie very close to that (32° C.) of 1,1-dichloro-1-fluoroethane.

SUMMARY OF THE INVENTION

A process has now been found which enables these impurities, chiefly 1,1-dichloroethylene and dichloroacetylene, to be removed, and thus a 1,1-dichloro-1-fluoroethane of excellent purity is obtained.

DETAILED DESCRIPTION OF THE INVENTION

The process according to the invention consists in subjecting crude 1,1-dichloro-1-fluoroethane to the action of chlorine and/or of a hydracid (HCl and/or HF). This treatment is effected in the presence of a Lewis acid or, but only in the case of chlorine, by photochemical catalysis, and in then distilling the product treated in this way.

A crude 1,1-dichloro-1-fluoroethane to be treated in accordance with the process according to the invention generally contains from 50 to 99.8% by weight of 1,1-dichloro-1-fluoroethane, from 0.1 to 0.3% of 1,1-dichloroethylene, from 0 to 25% of 1,1,1-trichloroethane and from 0.1 to 25% of 1-chloro-1,1-difluoroethane, and also traces of unsaturated compounds such as dichloroacetylene (approximately 10–20 ppm). In addition, it contains dissolved hydrochloric and hydrofluoric acids. Of course, it would not constitute a departure from the present invention to apply this treatment to a crude product containing less than 0.1% of 1,1-dichloroethylene or containing up to approximately 10% thereof.

In the description which follows, the operating conditions are defined in relation to 1,1-dichloroethylene. This impurity is the most important one.

The quantity of chlorine and/or hydracid to be used depends first on the content of 1,1-dichloro-ethylene in the crude 1,1-dichloro-1-fluoroethane to be treated. It also depends on the Lewis acid which may be employed as catalyst. It is known, in fact, that an antimony catalyst, for example, is active only in the $Sb^{+5}$ state and tends to be reduced to $Sb^{+3}$ by olefins, so that a minimum quantity of chlorine is necessary to keep a catalyst of this kind in its active form for performing the chlorination and/or hydrochlorination or hydrofluorination reactions. The molar ratio:

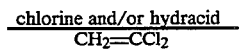

is preferably at least equal to 1.2. It may go up to 10 and is advantageously between 3 and 7. The chlorine and/or the hydracid may be introduced in the gaseous or liquid state directly into the crude product to be treated or predissolved in a fraction of the crude product to be treated.

The operation can be carried out at a temperature ranging from −20 to +70° C. However, it is preferably carried out below 35° C., advantageously between −5° and 30° C., so as to avoid the decomposition of 1,1,1-trichloroethane which may be present in the crude product to be treated and/or formed during the treatment.

The operation can be carried out at atmospheric pressure or at a pressure of up to 25 bars; but under industrial conditions, it is advantageously performed at a pressure of between 5 and 15 bars.

Although the treatment according to the invention can be carried out using photochemical catalysis (daylight or UV irradiation) for chlorine, the operation is preferably carried out in the presence of a catalyst consisting of a Lewis acid such as, for example, $FeCl_3$, $SbCl_5$, $TaF_5$, $TiCl_4$, $MoCl_5$, $SnCl_4$, $NbF_5$, and the like. The proportion of catalyst may vary from 0.001 to 1% by weight relative to the crude product to be treated.

The process according to the invention may be carried out noncontinuously, but under industrial conditions it is preferred to operate continuously. The length of the treatment can vary within wide limits. It depends not only on the initial content of 1,1-di-chloroethylene in the crude 1,1-dichloro-1-fluoroethane to be treated and the operating conditions used; but also on the efficiency which is required (more or less complete removal of 1,1-dichloroethylene), which can be easily monitored by taking samples and analyzing them by chromatography. Purely by way of guidance, a virtually complete removal of 1,1-dichloroethylene can be obtained within a time interval ranging from a few minutes (with $SbCl_5$) to a few hours (with $FeCl_3$).

When the treatment is finished, it suffices, after a possible separation of the catalyst, to distill the product to obtain a 1,1-dichloro-1-fluoroethane of excellent purity. This distillation, intended to separate 1,1-dichloro-1-fluoroethane from the lighter or heavier compounds initially present and/or formed during the treatment, is preferably carried out at atmospheric pressure, but may also be carried out at super- or subatmospheric pressure.

When the treatment according to the invention has been performed in the presence of a catalyst, the latter may be separated off, before the distillation, by alkaline or basic washing or may be complexed by a Lewis base such as, for example, a trialkyl or triaryl phosphate, an alcohol or water.

EXAMPLES

The following examples illustrate the invention without limiting it:

EXAMPLE 1

95 g of a mixture comprising 0.81 moles of 1,1-dichloro-1-fluoroethane and $3.1 \times 10^{-3}$ moles of 1,1-dichloroethylene are placed in a round-bottom flask of blackened glass. While this mixture is at 0° C. and being stirred, 1.2 g of chlorine and 0.25 g of antimony pentachloride are added to it abruptly. Ten minutes after this addition, a sample is taken to which a little sodium arsenite is added to stop any progress of the reaction until the determination, performed by gas chromatography.

The following results are obtained:

TABLE 1

|  | COMPOSITION (in % by weight) Initial | after treatment |
|---|---|---|
| 1,1-Dichloro-1-fluoroethane | 99.68 | 94.53 |
| 1,1-Dichloroethylene | 0.32 | <0.01 |
| 1-Chloro-1,1-difluoroethane |  | 2.14 |
| 1,1,1-Trichloroethane |  | 2.41 |
| Trichloroethylene |  | 0.14 |
| 1,1,1,2-Tetrachloroethane |  | 0.77 |

In addition to the disappearance of 1,1-dichloroethylene, a partial disproportionation of 1,1-dichloro-1-fluoroethane to 1-chloro-1,1-difluoroethane and to 1,1,1-trichloroethane is observed, together with a slight chlorination of the latter compound to tetrachloroethane.

1,1-Dichloro-1-fluoroethane can then be readily separated from other constituents by fractional distillation of the mixture.

EXAMPLE 2

The following are used, the operation being carried out in the same apparatus as in Example 1 and at the same temperature (0° C.):

- 82 g of a mixture comprising 0.7 moles of 1,1-dichloro-1-fluoroethane and $2.1 \times 10^{-3}$ moles of 1,1-dichloroethylene,
- 1 g of chlorine, and
- 0.5 g of FeCl$_3$.

The chromatographic analyses performed as a function of time (t), after stopping the reaction, gave the following results:

TABLE 2

|  | COMPOSITION (% by weight) at time t (minutes) | | | |
|---|---|---|---|---|
|  | t = 0 | t = 30 | t = 60 | t = 180 |
| 1,1-Dichloro-1-fluoroethane | 99.75 | 99.66 | 99.64 | 99.64 |
| 1,1-Dichloroethylene | 0.25 | 0.12 | 0.05 | 0.01 |
| 1-Chloro-1,1-difluoroethane- | traces | traces | traces | traces |
| Trichloroethylene |  | 0 | 0.02 | 0.05 |
| 1,1,1,2-Tetrachloroethane |  | 0.22 | 0.29 | 0.30 |

EXAMPLE 3

The procedure uses the same apparatus as in Example 1, but the operation is carried out at approximately 29° C. with the following quantities:

- 98.07 g of a mixture comprising 97.9 g of 1,1-dichloro-1-fluoroethane and 0.17 g of 1,1dichloroethylene,
- 0.8 g of chlorine, and
- 0.42 g of FeCl$_3$.

Chromatographic analysis carried out after stopping the reaction gave the following results:

TABLE 3

|  | COMPOSITION (in % by weight) Initial (t = 0) | after treatment (t = 30) |
|---|---|---|
| 1,1-Dichloro-1-fluoroethane | 99.83 | 99.70 |
| 1,1-Dichloroethylene | 0.17 | none (well below 0.01) |
| 1-Chloro-1,1-difluoroethane | traces | traces |
| Trichloroethylene |  | 0.05 |
| 1,1,1,2-Tetrachloroethane |  | 0.25 |

EXAMPLE 4

500 g of 1,1-dichloro-1-fluoroethane containing 46.5 mg of dichloroacetylene are placed in a glass reactor with stirring at 16° C., and 800 mg of SbCl$_5$ and 0.3 g of chlorine are then added. Analysis of the mixture after 15 minutes shows that dichloroacetylene has disappeared completely and has been converted chiefly into 1,2-dichloroethylene.

EXAMPLE 5

2,167 g of industrial 1,1-dichloro-1-fluoroethane are placed in a reactor made of blackened glass, kept stirred and at 15°–16° C., and 600 mg of FeCl$_3$ are added. Chlorine is then introduced using a dip tube, at a rate such that the dissolved chlorine content is kept at approximately 5 g/l.

The following table gives the initial composition and that measured after 6 hours' reaction:

TABLE 4

|  | COMPOSITION (in % by weight) | |
|---|---|---|
|  | Initial | After 6 hours |
| 1,1-Dichloro-1-fluoroethane | 89.80 | 86.15 |
| 1-Chloro-1,1-difluoroethane | 1.38 | 1.46 |
| 1,1-Dichloroethylene | 6.00 | ≦0.01 |
| 1,1,1-Trichloroethane | 2.32 | 2.40 |
| Trichloroethylene | 0.50 | 0.78 |
| 1,1,1,2-Tetrachloroethane | — | 8.00 |
| Pentachloroethane | — | 1.20 |
| Dichloroacetylene | 20 ppm | ≦1 ppm |

2.5 g of tributyl phosphate are added to the reaction mixture obtained after 6 hours' reaction, and a distillation is then carried out. After removal of the head and tail fractions, 1,600 g of 1,1-dichloro-1-fluoroethane with a purity higher than 99.5% are recovered.

EXAMPLE 6

100 g of crude 1,1-dichloro-1-fluoroethane containing 0.13% by weight of 1,1-dichloroethylene are placed in a receptacle lit by a daylight lamp. With the temperature brought up to and kept at 20°–22° C., chlorine is introduced to bring the dissolved chlorine content to approximately 7 g/l.

Chromatographic analysis of the reaction mixture shows that the 1,1-dichlorethylene content (initially 0.13%) changes to 0.06% after 60 minutes and to 0.02% after 120 minutes.

By way of comparison, when the operation is carried out in the same way in the absence of chlorine the 1,1-dichloroethylene content remains unchanged, even after 4 hours' irradiation.

EXAMPLE 7

100 g of 1,1-dichloro-1-fluoroethane containing 0.22% by weight of 1,1-dichloroethylene are placed in a reactor and 210 mg of $FeCl_3$ are then added. The mixture is cooled to $-3°$ C. and is saturated with HCl gas.

After 2 hours the chromatographic analysis of a sample shows a concentration of 0.13% of 1,1-dichloroethylene and the appearance of a 1,1,1-trichloroethane peak.

The test is continued for 10 hours, and it is found that the concentration of 1,1-dichloroethylene is then 0.05%.

EXAMPLE 8

100 g of 1,1-dichloro-1-fluoroethane containing 0.14% by weight of 1,1-dichloroethylene are placed in a reactor. This is cooled to $-10°$ C. and 400 mg of $SbCl_5$ are then added and the mixture is saturated with HCl gas.

After one hour, a sample shows that the concentration of 1,1-dichloroethylene is below 0.02%. 1,1,1-Trichloroethane and 1-chloro-1,1-difluoroethane appear on the chromatogram.

EXAMPLE 9

A reaction offtake at a rate of 100 liters/hour from a manufacture of 1,1-dichloro-1-fluoroethane and of 1-chloro-1,1-difluoroethane is taken to a pressure of 10 bars gauge and to a temperature of 9° C. for approximately 3 hours, while a very small quantity of chlorine (approximately 200 g/h) is injected to keep the $SbCl_5$ catalyst in its active form.

The initial and final compositions by weight are shown in the following table:

TABLE 5

| COMPOSITION: | Initial | Final |
|---|---|---|
| Saturated organic products (*) | 97% | 97.3% |
| 1,1-Dichloroethylene | 2,500 ppm | ≦70 ppm |
| Dichloroacetylene | 10–20 ppm | ≦1 ppm |
| $SbCl_5$ | 7,200 ppm | 7,200 ppm |
| HCl + HF | 2% | 1.9% |

(*) Chiefly, 1,1-dichloro-1-fluoroethane, 1-chloro-1,1-difluoroethane and 1,1,1-trichloroethane In this example, the high content of hydracids (HCl+HF), the pressure and the low temperature have made possible the reverse change of the unsaturated products into saturated products, in the presence of the $SbCl_s$ catalyst, whose activity has been maintained by injecting chlorine.

EXAMPLE 10

A 315 cm$^3$ reactor made of blackened glass is used, fitted with a stirrer and equipped for operating continuously. It is immersed in a fluid kept at a constant temperature and comprises an overflow, a temperature sensor, means for introducing liquid and gas feed through a dip tube, a reflux condenser kept at $-15°$ C. and, situated in the center of the reactor and partly masked to control the luminous flux, a 75-watt high pressure lamp of the "luminous sign" type.

Continuous test of purification of 1,1-dichloro-1-fluoroethane containing olefinic products are carried out. Chlorine is introduced into a vessel stock consisting of 1,1-dichloro-1-fluoroethane to be purified, up to the desired concentration (double the quantity needed to chlorinate the olefins present). Then the lamp is switched on, and impure 1,1-dichloro-1-fluoroethane and chlorine are injected continuously using a metering pump. The unit is brought up to a steady state over approximately 3 to 3.5 hours and then balances are determined during 2 hours, comprising the measurement of the flow rates, that of the chlorine dissolved in the effluent and the analysis of the organic products by liquid chromatography.

Three tests were thus carried out under the operating conditions and with the results summarized below.

TABLE 6

| | Test A | Test B | Test C |
|---|---|---|---|
| Illumination: | | | |
| watt/liter | 1 | 2 | 2 |
| cm$^2$/liter | 11 | 22 | 22 |
| Temperature (°C.) | 15 | 16 | 16 |
| Impure 141b flowrate (ml/h) | 318 | 207 | 318 |
| Residence time (min.) | 59 | 91 | 59 |
| Chlorine dissolved in the effluent (mole/liter) | 0.052 | 0.055 | 0.0335 |
| Dichloroethylene (weight %) | | | |
| entry | 0.58 | 0.58 | 0.56 |
| exit | 0.19 | 0.014 | <0.005 |
| Dichloroacetylene (weight %) | | | |
| entry | — | — | 0.11 |
| exit | — | — | <0.005 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the purification of a crude 1,1-dichloro-1-fluoroethane containing 1,1-dichloroethylene and/or dichloroacetylene comprising treating the crude 1,1-dichloro-1-fluoroethane with chlorine and/or HCl in the presence of a compound having catalytic activity consisting of $SbCl_5$ or $FeCl_3$ at a temperature between about $-5$ and about $+30°$ C., and at a pressure less than about 25 bars and then distilling the product treated in this way, substantially removing the 1,1-dichloroethylene and/or the dichloroacetylene from the 1,1-dichloro-1-fluoroethane, said chlorine and/or HCl acting to maintain the catalytic activity of said $SbCl_5$ or $FeCl_3$ during said purification.

2. Process according to claim 1, wherein the molar ratio

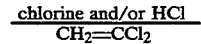

is between 1.2 and 10.

3. Process according to claim 2, wherein the molar ratio is between 3 and 7.

4. Process according to claim 1, wherein $SbCl_5$ or $FeCl_3$ is employed in a proportion ranging from 0.001 to 1% by weight relative to the crude product to be treated.

5. Process according to claim 1, wherein the treatment is carried out continuously.

6. Process for the purification of a crude 1,1-dichloro-1-fluoroethane according to claim 1, wherein HF is also present during treatment of the crude 1,1-dichloro-1-fluoroethane.

* * * * *